US008634896B2

(12) United States Patent
Sra et al.

(10) Patent No.: US 8,634,896 B2
(45) Date of Patent: Jan. 21, 2014

(54) 3D MODEL CREATION OF ANATOMIC STRUCTURES USING SINGLE-PLANE FLUOROSCOPY

(75) Inventors: Jasbir Sra, Pewaukee, WI (US); Stephen J. Merrill, Racine, WI (US)

(73) Assignee: APN Health, LLC, Pewaukee, WI (US)

( * ) Notice: Subject to any disclaimer, the term of this patent is extended or adjusted under 35 U.S.C. 154(b) by 194 days.

(21) Appl. No.: 12/885,710

(22) Filed: Sep. 20, 2010

(65) Prior Publication Data

US 2012/0071751 A1   Mar. 22, 2012

(51) Int. Cl.
A61B 5/05   (2006.01)

(52) U.S. Cl.
USPC ............................................. 600/424

(58) Field of Classification Search
USPC ............................................. 600/424
See application file for complete search history.

(56) References Cited

U.S. PATENT DOCUMENTS

| 7,778,690 | B2 | 8/2010 | Boese et al. | |
| 2003/0220555 | A1 | 11/2003 | Heigl et al. | |
| 2005/0020911 | A1* | 1/2005 | Viswanathan et al. | 600/424 |
| 2005/0256398 | A1* | 11/2005 | Hastings et al. | 600/423 |
| 2006/0241465 | A1 | 10/2006 | Huennekens et al. | |
| 2007/0106146 | A1* | 5/2007 | Altmann et al. | 600/407 |
| 2008/0043902 | A1 | 2/2008 | Viswanathan | |
| 2008/0152205 | A1 | 6/2008 | Vaillant et al. | |
| 2009/0208079 | A1 | 8/2009 | Vaillant et al. | |

OTHER PUBLICATIONS

Dictionary definition of "assumption" from dictionary.com.*
Dictionary definition of "measuring" from dictionary.com.*
Wittkampf, F.H.M. et al. "LocaLisa: New Technique for Real-Time 3-Dimensional Localization of Regular Intracardiac Electrodes." Journal of the American Heart Association, 99:1312-1317. Date: Copyright 1999.
Carto XP Electroanatomical Navigation System brochure. Biosense Webster. Date: Copyright 2004.
Bhakta, D. et al. "Principles of Electroanatomic Maping." Indian Pacing and Electrophysiology Journal, 8(1): 32-50. Date: 2008.

* cited by examiner

Primary Examiner — Jonathan Cwern
(74) Attorney, Agent, or Firm — Jansson Munger McKinley & Shape Ltd.

(57) ABSTRACT

A method for 3D reconstruction of the positions of a catheter as it is moved within a human body, comprising: (a) ascertaining the 3D position of a point on a catheter for insertion into the body; (b) acquiring fixed-angle, single-plane fluoroscopic image data of the body and catheter; (c) transferring the image data and catheter-point position to a computer; (d) determining 2D image coordinates of the point on the catheter; (e) changing the insertion length of catheter by a measured amount; (f) acquiring additional single-plane fluoroscopic image data of the body and catheter from the same angle, transferring the length change and image data to the computer, and determining image coordinates of the point on the catheter; (g) computing the 3D position of the catheter point; and (h) repeating steps e-g. A 3D model is constructed by assembling the plural 3D positions of the catheter point.

9 Claims, 10 Drawing Sheets

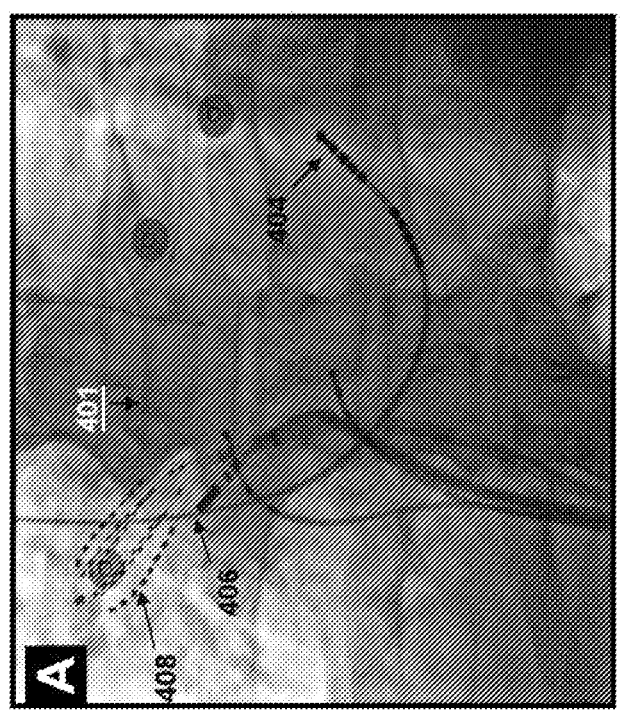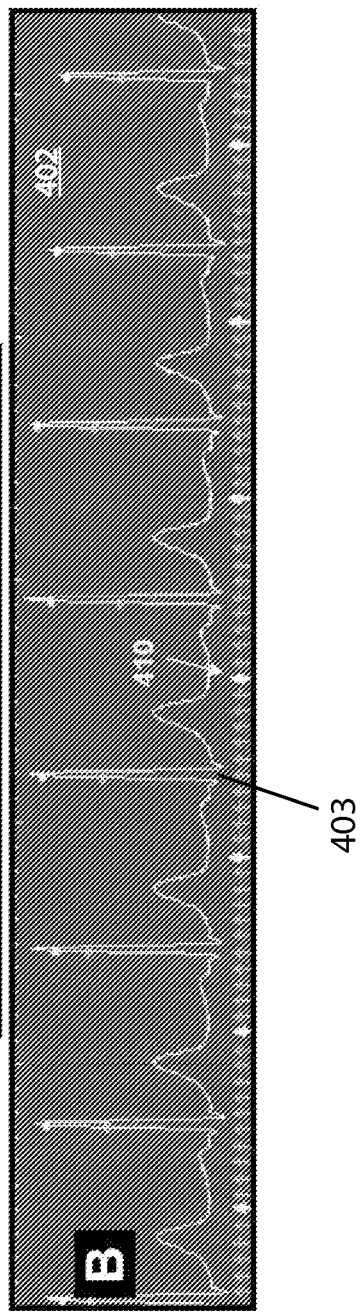
FIG. 3A
FIG. 3B

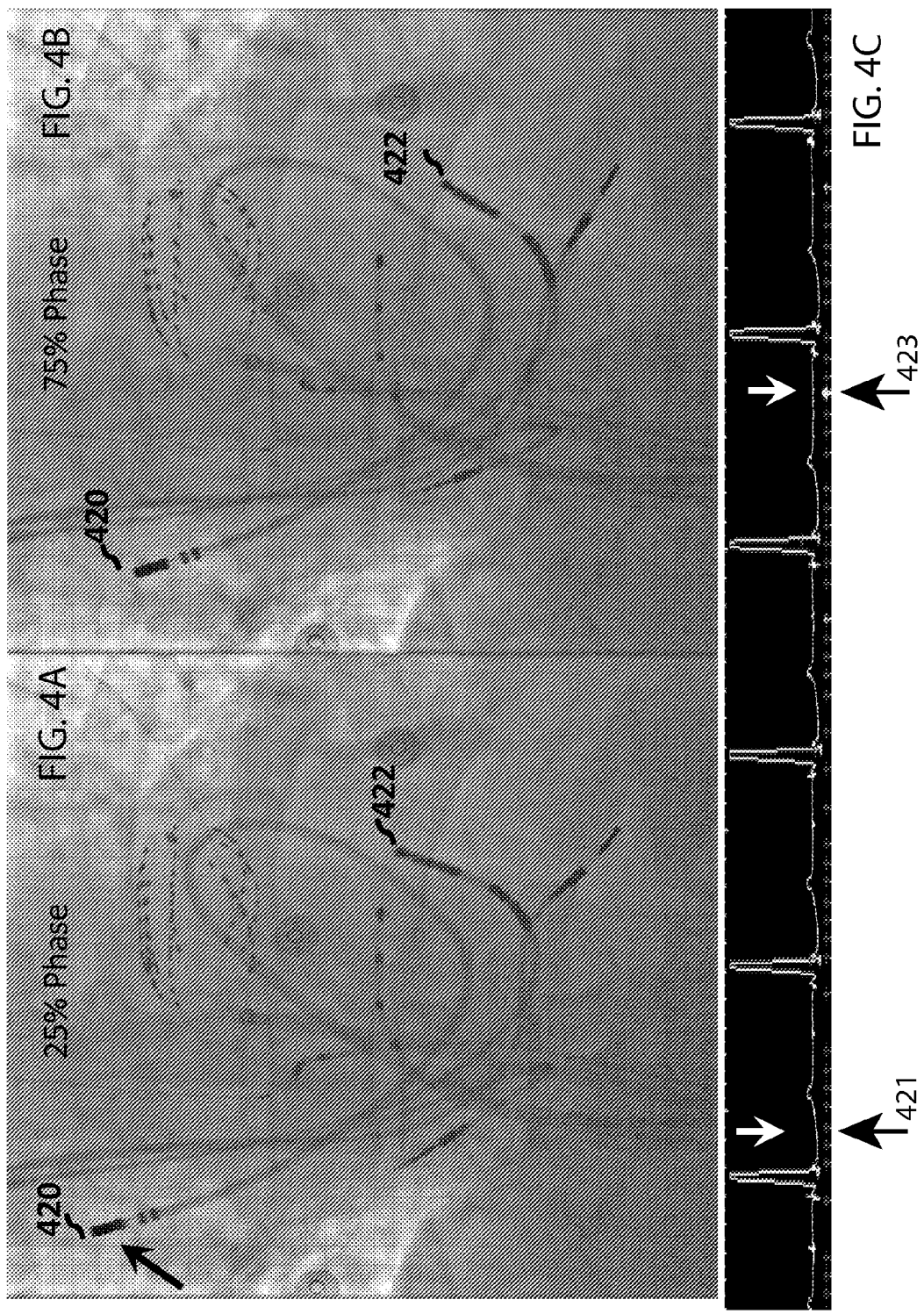

3D MODEL CREATION OF ANATOMIC STRUCTURES USING SINGLE-PLANE FLUOROSCOPY

FIELD OF THE INVENTION

The present invention generally relates to the field of medical imaging and more particularly to three-dimensional image creation using imaging only from 2D fluoroscopy.

BACKGROUND OF THE INVENTION

Anatomical mapping systems provide the three-dimensional (3D) position of a navigational catheter within the cardiac chamber of interest and, in some instances, can also be used to construct 3D maps of the cardiac chamber. Systems such as CARTO (Biosense Webster, Diamond Bar, Calif.) use the electromagnetic position of the catheter tip relative to an electromagnetic locator pad which is placed below the patient and a reference catheter at a fixed external (usually posterior) location. LocaLisa (Medtronic, Minneapolis) and NavX (St. Jude's Medical, Minneapolis, Minn.) systems use voltage gradients generated by external electrical fields to spatially orient and localize the catheter tip. The EnSite system (St. Jude's Medical) uses an electrically-coded catheter and a multi-electrode mapping balloon to create maps and define the location of the navigational catheter. The CARTO, Ensite, LocaLisa, and NavX systems have been used to create 3D maps of the left atrium (LA) and will be described in more detail.

The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of a magnetic field emitter mounted under the patient, a location sensor inside the mapping and ablation catheter tips, and a data processing unit and graphical display unit to generate and display the 3D model of the cardiac chamber of interest. Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, yaw, and pitch. The position and orientation of the catheter tip can be seen on the screen and monitored in real time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Non-contact mapping using the EnSite system is based upon the premise that endocardial activation creates a chamber voltage field which obeys LaPlace's equation. The EnSite system includes of a multi-electrode balloon which is placed inside the heart chamber of interest. The balloon or multi-electrode array is comprised of a braid of 64 polyamide-insulated, 0.003 mm diameter wires. For electrophysiologic studies, any mapping catheter can be used. The catheter location system uses a low-level, 5.68 kHz current emitted by a distal electrode which returns to each of two intrachamber ring electrodes on the multi-electrode array. Since the position of both the array electrodes and the current sink electrodes are known, a custom algorithm determines the position of the roving catheter by demodulating the 5.68 kHz potentials. The mapping catheter is moved around the chamber to create a 3D map. A high-resolution activation and 3D map can be created using custom-built algorithms. The EnSite system, like the CARTO system, has been used to treat arrhythmias including atrial fibrillation, atrial flutter, atrial tachycardias and ventricular tachycardias. Again, like the CARTO system, the EnSite system is very expensive, its resolution depends on the number of points taken, and a fluoroscopic system is commonly used to confirm the location of catheters.

The LocaLisa system uses 1 mA-current-generated electromagnetic fields at approximately 30 kHz, emitted from cutaneous patches placed on the subject's chest. These patches are positioned to create a 3D axis system. In addition to the connection of the position reference catheter and a mapping-ablation catheter, the LocaLisa system provides several other channels on which recordings can be made from several different catheters. Catheters in the subject's heart receive these signals, and the position of the catheter can be determined. One limitation of the LocaLisa system is that it merely provides the user with information about the catheter position—no geometric anatomical model can be created.

The NavX system, in addition to having all of the features of the LocaLisa system, can also, similar to the CARTO system, create activation maps and 3D anatomical maps of the chamber of interest. As described above, these technologies have several limitations. As in other electroanatomic mapping systems, the accuracy of the chamber reconstruction process is directly dependent upon the number of the points taken and the position of the catheter. Another significant limitation is that the heart is essentially considered a rigid body over which maps such as activation map are displayed. Also, cardiac chamber distortion due to cardiac and respiratory motion is not taken into account if a significant change in heart rate occurs from the time the map was created to the time therapy is delivered. However, the biggest drawback, as described before, is that these systems are expensive, require separate mapping systems, and do not provide real-time visualization of the chamber. Consequently, fluoroscopy is used almost all the time to confirm location of the system.

Fluoroscopy is used in all cardiac labs to identify location of catheters and other interventional instruments such as leads, stents, or other instruments. However, in the past, fluoroscopy has not been used to create 3D maps since it provides only two-dimensional images. Furthermore, unlike anatomical systems described before, anatomical maps, electrical maps and voltage maps cannot be created by currently-available fluoroscopy systems.

This invention resolves these issues by providing a system which creates a 3D model using only single-plane fluoroscopic images and a catheter as it is moved around the heart chamber of interest. Furthermore, activation maps, electrical maps and voltage maps can be created on this 3D model, and the location of catheter marked as needed.

Fluoroscopy is used to visualize body organs and structures such as bones. Since it is available in all labs to navigate catheters, sheaths, and the like, the present invention uses this imaging technique to create 3D maps which in the past have not been created due to two-dimensional modality of the fluoroscopy imaging system. In a fluoroscopic system, the X-ray generator allows selection of the voltage and current delivered to the X-ray tube. Two methods, continuous and pulsed exposure, are used for fluoroscopy. During continuous fluoroscopy, the generator provides steady tube current. Images are usually acquired at a rate of 30 frames per second, resulting in an acquisition time of 33 milliseconds (msec) per image. During pulsed fluoroscopy, for example, a frame rate such as 30 frames per second may be used with each exposure having a short duration of 3 to 10 msec. Thus, heart-cycle-gated fluoroscopy imaging may, for example, use pulses of 3 to 10 msec in duration only at predetermined phase (such as diastole), thus improving the resolution and reducing radiation exposure.

OBJECTS OF THE INVENTION

It is an object of the present invention to provide a medical imaging system which creates 3D models of the heart by identifying the various positions of a catheter within 3D anatomical structures such as cardiac chambers using only a single-plane fluoroscopic system, thus overcoming many of the shortcomings of the prior art imaging systems discussed above.

It is a further object of the present invention to provide a medical imaging system which reconstructs the position of a catheter within 3D cardiac structures and generates three-dimensional models of anatomical structures without the use of costly systems such as CT scanners or MRI systems and other mapping systems such as electroanatomic mapping systems.

Another object of the present invention is to provide a medical imaging system which reconstructs the position of a catheter and generates three-dimensional models of anatomical structures using readily-available medical equipment.

Yet another object of the present invention is the provide a medical imaging system which improves the accuracy and therefore the effectiveness of medical procedures without the use of systems such as CT scanners or MRI systems and other expensive mapping systems.

It is a further object of the present invention to provide a medical imaging system which can be used to identify the location of the catheter in an x,y,z coordinate system using only single-plane fluoroscopy.

SUMMARY OF THE INVENTION

As used herein, the term "point on a catheter" refers to any identifiable point on a catheter used in a medical procedure in conjunction with fluoroscopic imaging. The most easily identifiable point, of course, is the tip of the catheter, but any identifiable point along the catheter (or catheters) may be used as a point-of-interest POI.

As used herein, the term "single-plane fluoroscopy" refers to operation of a fluoroscopy system at a fixed angle such that all images taken during a procedure are taken from the same (i.e., fixed) angle.

The present invention is a method for the 3D reconstruction of the positions of a catheter as it is moved within a region of the human body, such as a cardiac chamber. The inventive method comprises the following steps: (a) ascertaining the 3D position of a point on a catheter for insertion in the body region; (b) acquiring a fixed angle, single-plane fluoroscopic image of the body region and of the catheter; (c) transferring the image data and catheter-point position to a computer; (d) determining the 2D image coordinates of the point on the catheter; (e) changing the length of catheter insertion by a measured amount; (f) thereafter acquiring a further single-plane fluoroscopic image of the chamber region and the catheter from the same angle, transferring the length change and additional image data to the computer, and determining the 2D image coordinates of the point on the catheter; (g) computing the 3D position of the catheter point; and (h) repeating steps e-g plural times.

In preferred embodiments of the inventive method, the point on the catheter is the tip of the catheter.

In some preferred embodiments, the fluoroscopic images are ECG-gated, and in some preferred embodiments, the fluoroscopic images are respiration-gated.

In highly-preferred embodiments of the inventive method, the method further includes the step of assembling the plural 3D positions of the point within the body region into a 3D model of the region. Some of these highly-preferred embodiments also include the step of displaying the 3D model on a graphics display, and some such embodiments include displaying the 3D model overlaid simultaneously on the fluoroscopic images as the images are transferred sequentially to the computer.

In several preferred embodiments, the method includes the further step of creating an electrical map over the 3D model and marking points in the 3D model as the catheter is moved over the 3D model.

In other preferred embodiments of the inventive method, the step of assembling the plural positions of the point within the body region into a 3D model further includes interpolating between such points.

DESCRIPTION OF THE DRAWINGS

FIG. 3A is an example fluoroscopic image acquired at a single phase of the heart and respiration cycle. FIG. 3B illustrates the ECG signal by which the image in FIG. 3A has been gated.

FIGS. 4A and 4B presents two fluoroscopic images illustrating how ECG gating is useful. FIG. 4C illustrates the ECG signal by which the images in FIGS. 4A and 4B have been gated.

FIG. 5 shows definitions of the x, y and z-axes of the procedural suite.

FIG. 10 also shows an overlaid electrical map which may be used to assist in interventional treatment.

DETAILED DESCRIPTION OF PREFERRED EMBODIMENTS

Figure 1:
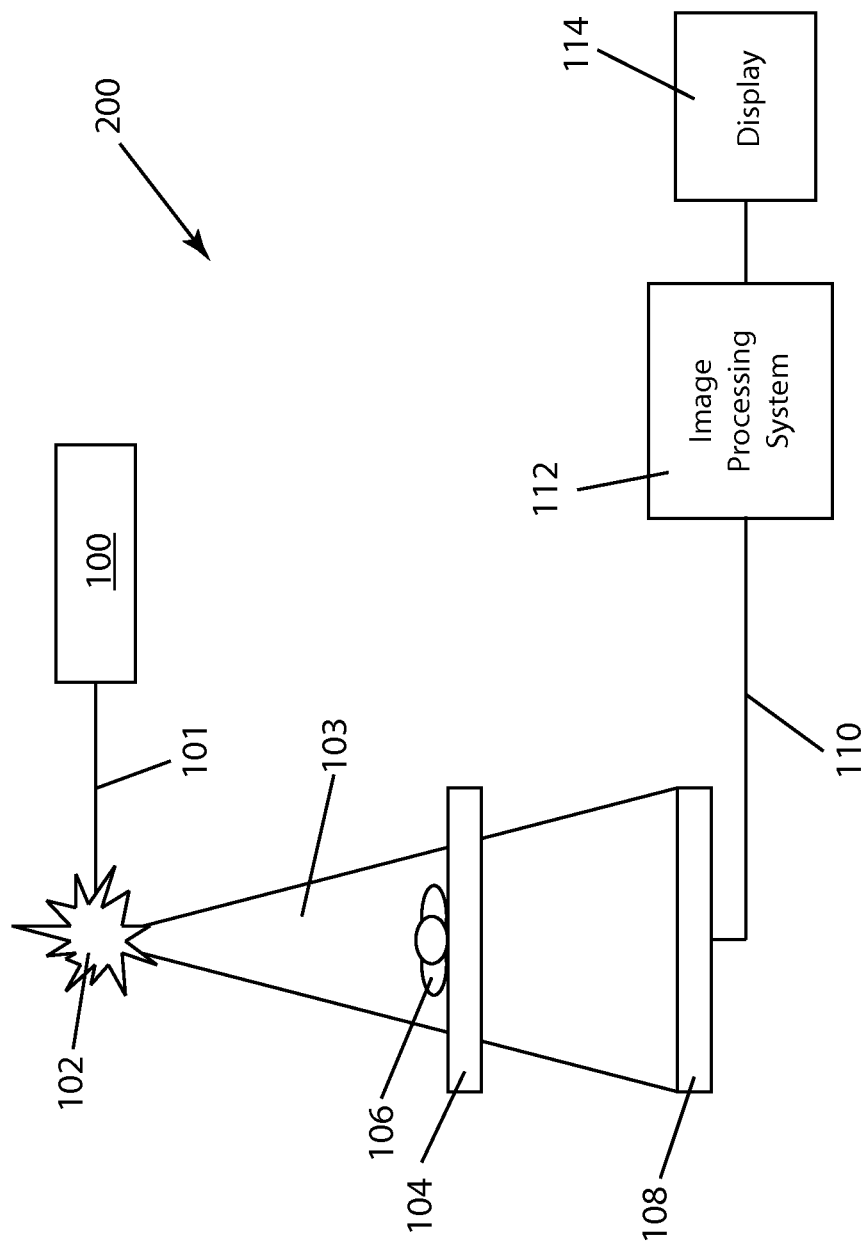
FIG. 1 is a schematic diagram of an X-ray imaging system used to carry out the inventive method of 3D model creation using fluoroscopy.

FIG. 1 illustrates the basic elements of a conventional fluoroscopy image acquisition system 200 used to acquire fluoroscopic image data. The imaging process for conventional fluoroscopy involves an X-ray tube 102 which sends an X-ray beam 103 through a patient 106 on a table 104. X-ray generation is initiated by pushing on a paddle 100 which is connected to the X-ray tube 102 by a communication link 101. A detector 108 includes an image intensifier (within detector 108) which receives the X-rays transmitted through patient 106 and transforms the X-ray energy into light. A video camera (also within detector 108) converts the light into an analog electrical signal which is then sent along communication link 110 to an analog-to-digital converter in an image processing unit 112. Image data operated on within image processing system 112 is then displayed on a computer display 114.

The process of cardiac and respiratory gating has been described in U.S. patent application Ser. No. 11/928,484 and Ser. No. 11/928,759, both filed on Oct. 30, 2007 and incorporated by reference herein. The gating process has been further described in U.S. patent application Ser. No. 12/455, 423 filed on Jun. 2, 2009 and incorporated herein by reference.

In brief, a fluoroscopy image acquisition system 200 (as depicted in FIG. 1) can provide gated fluoroscopic images in two different ways. In one technique, fluoroscopic images are transferred to the computer workstation, and only images at the appropriate phase of the cardiac or respiratory cycle are analyzed and used for further evaluation. This technique involves a much higher exposure to radiation than a second technique depicted in FIG. 2.

Figure 2:
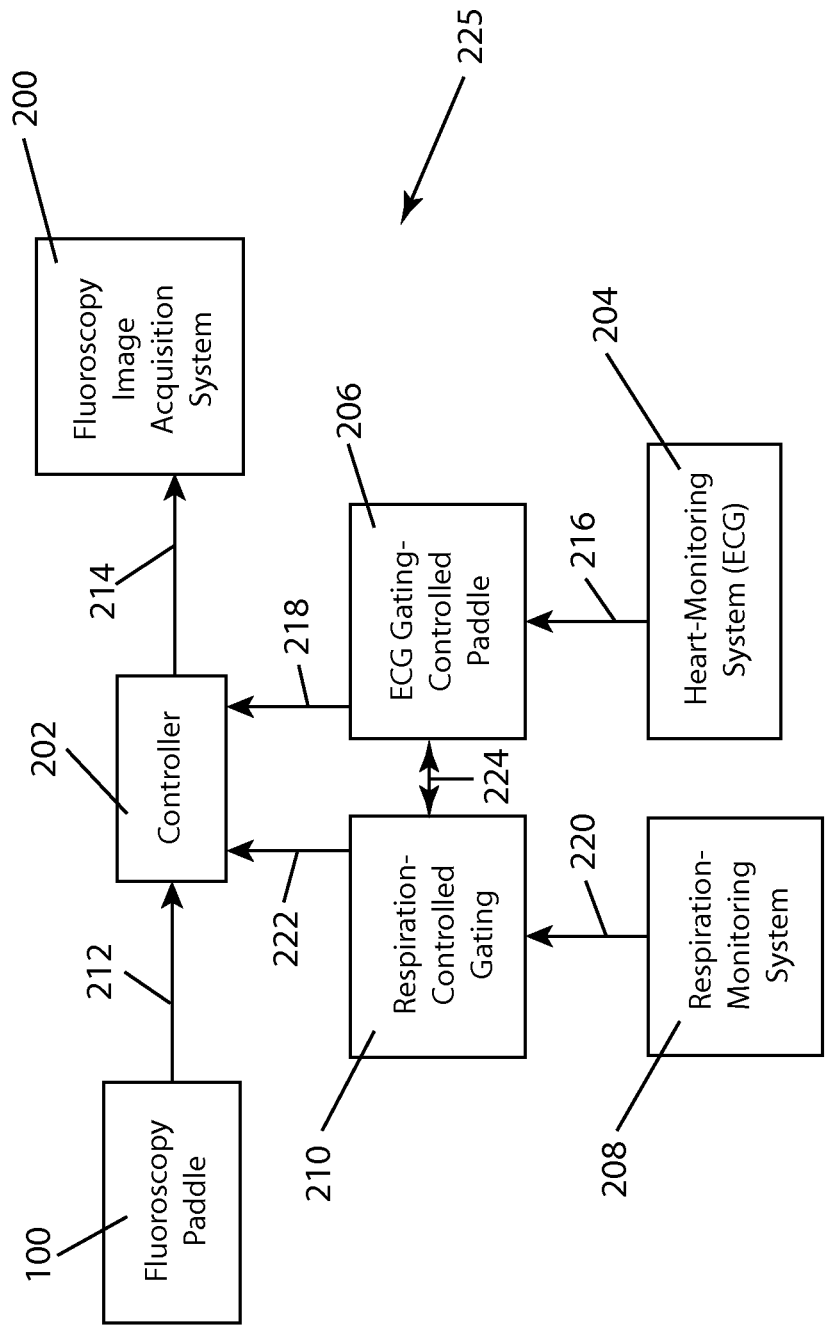
FIG. 2 is a functional schematic diagram of a fluoroscopy image acquisition using ECG and respiration gating.

Referring to FIG. 2, a functional schematic diagram of a system 225 for acquiring fluoroscopic images at predetermined gated cardiac and/or respiratory phases is shown. System 225 includes fluoroscopy image acquisition system 200 from FIG. 1 and several additional system elements to carry out gated image acquisition. Paddle 100 communicates with acquisition system 200 through the communication link 212 to a controller 202 and communications link 214. System 225 can function in a fashion similar to system 200 of FIG. 1 with the use of paddle 100 through controller 202. However, system 225 also includes a heart-monitoring system 206 which utilizes a patient's ECG signal (not shown in this figure) and a respiration-monitoring system 208 which captures a respiration signal (not shown) from a patient. Heart-monitoring system 204 is linked by communication link 216 to an ECG gating-controlled paddle (second paddle) which communicates with controller 202 through communication link 218. Respiration-monitoring system 208 is linked through communication link 220 to a respiration-controlled gating system 210 which communicates with controller 202 through communication link 222. System 225 is configured to allow the sharing of information between the cardiac gating and respiration gating portions of system 225, and this sharing is represented by an interconnecting communication link 224.

Controller 202 is programmable in order to enable system 225 to acquire fluoroscopic images just with paddle 100 control or with any combination of control using ECG-controlled gating, respiration-controlled gating, and manual control. Controller 202 may be located in a separate physical unit or may be realized with computational capabilities distributed over one or more of the other elements in system 225 which may contain computational capability, such as, but not limited to, fluoroscopy image acquisition system 200, heart-monitoring system 204 or respiration-monitoring system 208.

For cardiac gating operation, heart-monitoring system 204 establishes a specific phase of the heart cycle. When paddle 206 is pushed, heart-monitoring system 204 enables a gating signal at this specific phase of the heart cycle through controller 202. Fluoroscopic image acquisition system 200 thus acquires images only during the phase of the heart cycle which has been established by heart-monitoring system 204. With such specific cardiac phase selected, even if paddle 206 is pushed on a continuous basis, fluoroscopic image acquisition system 200 is activated during the specific phase of the cardiac cycle for a few milliseconds (e.g., 3 to 10 msec) to acquire a very short-duration image.

Again referring to FIG. 2, in addition to ECG gating, respiration gating can also be performed to produce appropriate images. In addition to heart-monitoring system 204, respiration-monitoring system 208 is also available in system 200, and information regarding the respiration cycle and the cardiac cycle are available for gating use. Controller 202 is further programmed to enable fluoroscopy image acquisition system 200 to acquire fluoroscopic images only during a specific respiration cycle phase or, more importantly, at a specific cardiac cycle phase during a specific respiration cycle phase. Thus, when paddle 206 is pushed while both cardiac-cycle gating and respiration-cycle gating are operational, fluoroscopic images are acquired only at a selected cardiac cycle phase and a selected respiration phase. Thus, both respiration gating and ECG gating can function together to make available high resolution fluoroscopic images for use in 3D model construction.

Although the images used herein are described predominantly at 75% of the heart cycle (diastole or relaxation phase of the heart), any phase of the heart cycle can be selected within the scope of the invention. For the purpose of triggering at the proper phase, either ECG signals or intracardiac recordings from any catheters placed inside the heart can be used.

FIGS. 3A and 3B illustrate cardiac-cycle gating of fluoroscopic image acquisition. FIG. 3A shows a fluoroscopic image 401 as it is displayed on display screen 114 of system 200. FIG. 3B shows an ECG signal 402 along a timeline, and ECG signal 402 has been used to control the gated acquisition of image 401. Also shown within image 401 are a catheter 404 placed inside the coronary sinus, an ablation catheter 406, and a multi-electrode basket catheter 408. As indicated in FIG. 3B by reference number 410, this image has been acquired at about 54% of the heart cycle. The 0% phase point of the cardiac cycle is indicated as the repeated peak points (the R-wave of the ECG signal) along the timeline in FIG. 3B; one such point is indicated by reference number 403. As previously explained, these images can also be acquired at a selected phase of the respiration cycle. For example, in addition to the images being ECG-gated, the system can be configured such that only images during the expiration phase or the inspiration phase (or any other phase of the respiration cycle) are acquired and displayed.

FIGS. 4A-4C present an example illustrating that gating is useful for the acquisition of high-resolution fluoroscopic images and therefore useful in the creation of 3D models in this invention. The fluoroscopic image in FIG. 4A is taken at 25% of the cardiac cycle as indicated by the white/black arrow pair 421 toward the left end of the ECG signal timeline in FIG. 4C. The catheters shown are mapping and ablation catheter 420 and coronary sinus catheter 422. On the right, FIG. 4B is a fluoroscopic image taken at 75% phase of the cardiac cycle as indicated by the white/black arrow pair 423 in FIG. 4C. Again shown are catheters 420 and 422. It can be appreciated that the location of each of these catheters in the two images is quite different. If various points in these fluoroscopic images to be used for creation of the 3D model are not taken at the same cardiac phase, the uncertainty of the measurements within such images could create substantial errors in the resulting 3D models, as will be seen in the description of 3D model creation below.

Alternatively, non-gated images can also be acquired for catheter location and orientation and creation of 3D models of anatomic structures.

The present invention involves applying the above-described fluoroscopic imaging techniques and systems, both motion-gated and non-motion-gated, to create three-dimensional models of anatomic structures. Data from two-dimensional fluoroscopic images, including the imaging of a point of interest (POI, e.g., the tip of a catheter) as it is navigated within these images, are processed using predetermined computational algorithms to create such 3D models. Imaging data only from 2D fluoroscopy is utilized to create the 3D models.

The inventive method uses data describing the movement of the POI by operator manipulation within single-plane fluoroscopy. The change in length of insertion of an inserted catheter and the observed movement of the tip of the catheter (POI) in a sequence of consecutive single-plane fluoroscopic images is used to determine the 3D coordinates of the POI. Multiple images taken in this fashion are combined to compute the path of the POI on the catheter and to create the 3D model of the chamber of interest, for example, the left atrium. This reconstructed model can then be used for interventional procedures such as atrial fibrillation ablation. Similarly, reconstruction of other cardiac chambers can be created, such as the right atrium and right and left ventricles for other interventions such as other ablations or device implantations. Further, the technique can also be used in other structures such as blood vessels, and other instruments such as leads and the like can be used for 3D model reconstruction.

Figure 5:
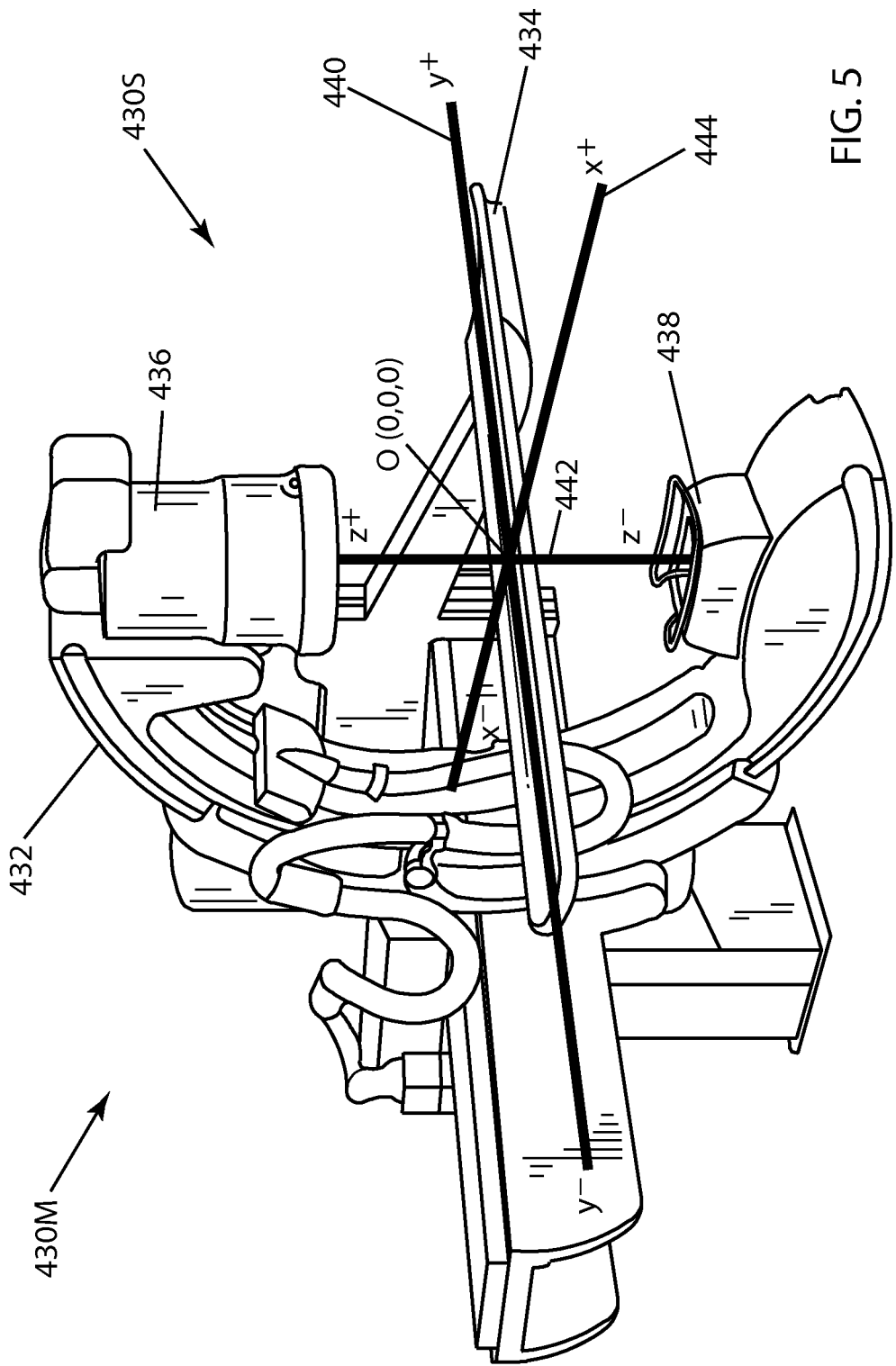
FIG. 5 is a perspective view of a typical X-ray machine such as is used in a procedural suite.

FIG. 5 is a typical view of an X-ray machine 430M used in a procedural (interventional) suite with a set of orthogonal x,y,z axes defined within the procedural suite. X-ray machine 430M includes a C-arm 432 which in FIG. 5 is shown in the anteroposterior (AP) position. X-ray machine 430M also includes a patient table 434 which is shown in a horizontal orientation which is typical for patient comfort. Referring to FIG. 5, with C-arm 432 in the AP position, a z-axis 442 is defined from an X-ray source 436 to the center of an image intensifier 438. X-ray table 434 also defines an x-axis 440 and a y-axis 444, both such axes being perpendicular to z-axis 442 and mutually perpendicular. The axes are shown by the heavy solid lines in FIG. 5. This set of machine axes thus defines a 3D procedural space 430S as indicated. FIG. 5 also illustrates the intersection of the axes, the center or origin O with coordinates (0,0,0) in the 3D procedural space 430S that is defined in the procedural suite. Space 430S and all its elements can now be viewed in terms of x,y,z coordinates. FIG. 5 further illustrates a sign convention for the axes, the positive and negative directions of each axis indicated by "+" and "−" superscripts on the axis nomenclature definitions.

With the 3D procedural space 430S thus defined, all positions of C-arm 432 and, consequently, X-ray source 436 and image intensifier 438 in space 430S, can be described using coordinates. Both X-ray source 436 and image intensifier 438 are at fixed distances from X-ray table 434.

It can be appreciated that x,y coordinates are discernible on a single-plane fluoroscopic image. However, without knowing the z-axis coordinate, it is not possible to identify the exact location of the tip of a catheter or other point of interest in three-dimensional space or to create 3D models of structures.

The inventive method for reconstructing the 3D coordinates of a POI along an inserted catheter (e.g., the catheter tip) using its position in a sequence of fluoroscopic images obtained at a single C-arm 432 position and measurements of the length of insertion of the catheter. This inventive approach uses only fluoroscopy as the imaging modality and is based on the concept that there is a correlation between change in actual length of catheter insertion and the distance moved by the POI observed on the sequential fluoroscopic images as the catheter is moved in 3D space. The fluoroscopic apparatus and procedural suite coordinate system described in FIG. 5 apply to this single C-arm position method.

Figure 6:
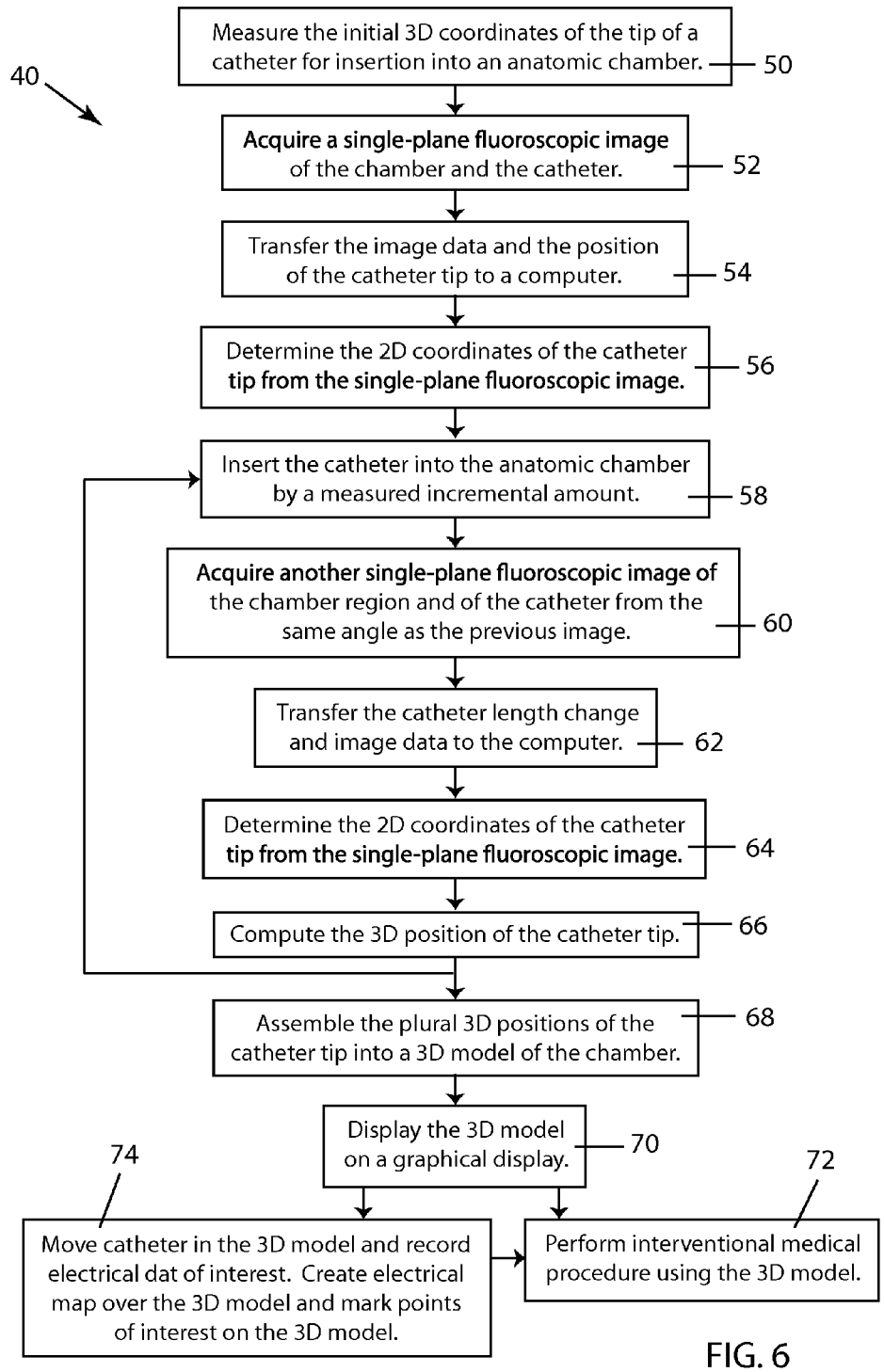
FIG. 6 is a schematic block diagram of one embodiment of the inventive method of 3D anatomic model creation using single-plane fluoroscopy.

FIG. 6 is a schematic block diagram of an embodiment 40 of the inventive method of creating a three-dimensional model of an anatomic chamber of interest (anatomic structure) using single-plane fluoroscopy. The embodiment of FIG. 6 uses fluoroscopic images from a fixed angle taken sequentially, and also uses data on the length of insertion of a catheter, apparatus which is part of the procedure.

At step 50, the initial 3D coordinates of the tip of the catheter are measured, the 3D coordinates being the coordinates in 3D space 430S. At step 52, a single-plane fluoroscopic image is acquired, the image including the region of the chamber of interest and the tip of the catheter. Image data and the position of the catheter tip are transferred to a computer at step 54. In step 56, the 2D image coordinates (in image intensifier 438) of the catheter tip are determined. Then, at step 58, the catheter tip is moved (inserted) an incremental amount and measured, and another single-plane fluoroscopic image of the chamber region and catheter tip is acquired (step 60) from the same angle as the initial image acquisition. This image and movement data are transferred to the computer at step 62. Again, the 2D image coordinates of the catheter tip are determined from the image data (step 64), and in step 66, the 3D position of the catheter tip is calculated.

This sequential operation, from incremental movement of the catheter tip in step 58 through determination of the 3D coordinates of the tip in step 66, is carried out repeatedly, thus generating a catheter-tip trajectory in 3D space 430S. This series of points (trajectory) in 3D space 430S is assembled at step 68 into a 3D model of the chamber of interest as the tip is moved. When a sufficient number of points on the trajectory are found, the spatial coordinates of the chamber of interest may thus be modeled and visualized in three dimensions.

In step 70, a graphical display is used to present the 3D model, which then may be used to assist in interventional medical procedures in step 72. In step 74, the displayed 3D model information may also be helpful in determining where to move the catheter tip in order to make various electrical measurements within the chamber of interest, and to enable particular points of interest to be marked for use in the interventional medical procedures.

Figure 7:
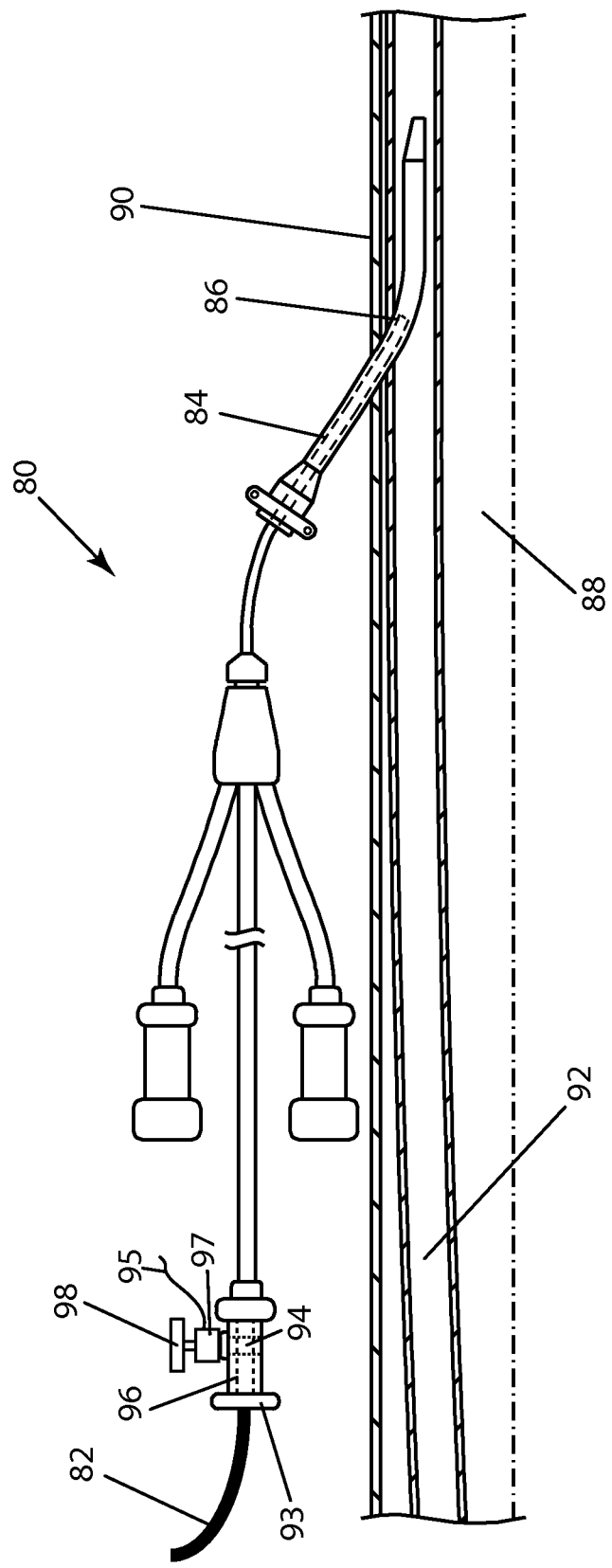
FIG. 7 is a schematic drawing illustrating the catheter insertion starting point and measurement of catheter insertion length.

FIG. 7 is a schematic drawing illustrating the determination of the initial 3D coordinates of the catheter tip as insertion of the catheter is started in step 50 of the embodiment of FIG. 6. Referring to FIG. 7, a sheath 80 is inserted into a vein 92 in the groin, neck, arm or other suitable anatomic structure (represented by reference number 88) with skin 90. Sheath 80 is used to guide the entry of a catheter 82 (only a small portion shown). A portion 84 of catheter 82 is represented by dotted lines within the end of sheath 80, and catheter tip 86 is also shown as part of portion 84. The 3D coordinates of catheter tip 86 are determined by direct measurement (e.g., independent of fluoroscopy) of the 3D position of sheath 80 and by knowing precisely how much of catheter 82 has been inserted into sheath 80. With catheter tip 86 in the fluoroscopic image at this initial 3D position, the starting position coordinates of tip 86 in 3D space 430S are determined.

FIG. 7 also shows one embodiment of apparatus to provide measurements of the incremental change in the inserted length of catheter 82. Sheath 80 includes a catheter entry 93 having an internal passage 96, a catheter drive cylinder 94, and a knob 98. Catheter 82 is pinched between catheter drive cylinder 94 and one side of internal passage 96 such that drive cylinder 94 frictionally moves catheter 82 in or out of sheath 80. When knob 98 is turned by a known angle, catheter drive cylinder 94 moves catheter 82 by a known incremental length. Catheter entry 93 also includes sensor 97 which measures the angle that drive cylinder 94 has been turned and transmits this data to the computer (not shown) via link 95. Sensor 97 may be an angle encoder of several types known to those skilled in the art of instrumentation.

In this inventive method, the following assumptions are made. At any given time t:
(a) the length of the inserted catheter, $l_c(t)$ (e.g., in millimeters), is known;
(b) the 2D fluoroscopy coordinates within image intensifier 438, $(p_x(t), p_y(t))$, of the POI are known; and
(c) the coordinates of the POI in 3D space 430S of the POI, $(x(t), y(t), z(t))$, are unknown.

A change $\Delta l_c(t)$ at time t in length of inserted catheter corresponds to a change in the x, y, z coordinates of the POI in 3D space 430S and with a change in the 2-D fluoroscopy image coordinates on image intensifier 438, as follows:

$$\Delta l_c(t) = l_c(t+\Delta t) - l_c(t),$$

$$(\Delta x(t), \Delta y(t), \Delta z(t)) = (x(t+\Delta t) - x(t), y(t+\Delta t) - y(t), z(t+\Delta t) - z(t)), \text{ and}$$

$$(\Delta p_x(t), \Delta p_y(t)) = (p_x(t+\Delta t), p_y(t+\Delta t)) - (p_x(t), p_y(t)).$$

And, $$\Delta l_c(t) = [(\Delta x(t))^2 + (\Delta y(t))^2 + (\Delta z(t))^2]^{1/2}$$

which yields:

$$\Delta z(t) = \pm[\Delta l_c(t)^2 - ((\Delta x(t))^2 + (\Delta y(t))^2)]^{1/2}$$

If $\Delta x(t)$ and $\Delta y(t)$ can be determined from $\Delta p_x(t)$ and $\Delta p_y(t)$, then $\Delta z(t)$ will be known. Then, for a series of time points $t_i = t_0, t_1, t_2, \ldots, t_n$, $\Delta x(t_i)$, $\Delta y(t_i)$, and $\Delta z(t_i)$ can be determined. Assuming knowledge of an initial 3D location, $(x(t_0), y(t_0), z(t_0))$, a time series of POI locations in 3D space 430S can be established for $i=1, 2, \ldots, n$.

Next, the relationship between $(\Delta x, \Delta y)$ and $(\Delta p_x, \Delta p_y)$ must be determined. As has been described above, fluoroscopic images are obtained as a projection of the POI from X-ray source $S_t$ (436) to image intensifier 438 having a center point at $I_t$. Based on the geometry, the location of the POI on the fluoroscopic image (image intensifier 438) depends on the distance of the POI from the center of projection of the X-ray.

To determine $(\Delta x, \Delta y)$ from $(\Delta p_x, \Delta p_y)$, a scale factor is computed based on the source-to-intensifier and object-to-intensifier ratio. The actual coordinates of the POI at t=0 are known, having been defined and measured at the beginning of a procedure, and the scale factor K is $$K = \frac{\text{distance of } POI \text{ to image intensifier 438 at } t = 0}{\text{distance from } X\text{-ray source 436 to image intensifier 438}}$$

The denominator is $h_1 + h_2$. (See FIG. 5C.) The scale factor is applied to $(\Delta p_x, \Delta p_y)$ to obtain reconstructed values for $(\Delta x, \Delta y)$.

Using the computed values for $(\Delta x, \Delta y)$, the absolute value of $\Delta z$ is computed. A determination of the sign of $\Delta z$ can be made in several ways. One such embodiment is to utilize the assumption that the physical nature of z(t) is such that it is a smooth curve, i.e., it has several continuous derivatives. The sign is then determined by estimating the derivatives by computing finite differences from the data available, as follows. At each time step $t_i$ values for $l_c(t_i)$ and $(\Delta z(t_i))^2$ are known as described above. If the previous value of the first difference, $\Delta z(t_{i-1})$, was greater than a threshold value $\delta$ for which $\delta > 0$ or smaller than $-\delta$, assume the same sign for $\Delta z(t_i)$ as for the previous value $\Delta z(t_{i-1})$. If this threshold condition is not satisfied, examine the computed second difference $\Delta z(t_{i-1}) - \Delta z(t_{i-2})$. Compare the second difference with a threshold in a fashion similar the threshold comparison of the first difference and choose the sign based on the derivative approximation. If these first two comparisons do not result in a sign selection, continue computing third and further differences until a sign is chosen.

From the above computations, a time sequence of values for the 3D coordinates of the POI is generated from time sequences of values for $\Delta l_c(t)$, $\Delta p_x(t)$, and $\Delta p_y(t)$ resulting in a 3D model of an anatomic region of interest.

Once the images are obtained from the fluoroscopic system, the fluoroscopic images are transferred to a computer having a graphics display. Any of the currently-available tools in the art can be used to create 3D computer graphics. The Visualization Toolkit (VTK) is an open-source, freely-available software system for 3D computer graphics, modeling, image processing, volume rendering, scientific visualization and information visualization. Such a computer graphics tool, in conjunction with a fluoroscopic imaging system (and, if desired, a catheter insertion-length measurement) can be adapted to carry out the methods described herein.

When the images are transferred to the computer workstation, linear interpolation can be used for the smoothing of adjoining data points in images. In 3D reconstruction, a sequence of discrete POI locations are acquired as described. Linear interpolation is then used for "filling in" the gaps between the reconstructed points.

Using this method, a 3D model of an anatomic chamber of interest may be constructed by creating a map of the boundary surface of this region. The steps for this process are: (1) identifying turning points in the position of the catheter (such points are on the boundary of the chamber); (2) building a mesh model of triangular elements based on known points from (1); (3) reconstructing the surface as it relates to nearby points as each new boundary point is added; and (4) repeating step (3) until the desired detail of the model is obtained.

In this process, turning points are identified as those points where one of the quantities Δx, Δy, or Δz changes sign. For the first two, the quantities are measured directly in the 2D fluoroscopic image. For Δz, a turning point is identified as a point where the first derivative approximation does not determine a sign of Δz, and further approximations were needed which resulted in a change of sign of Δz from preceding values.

Figure 8:
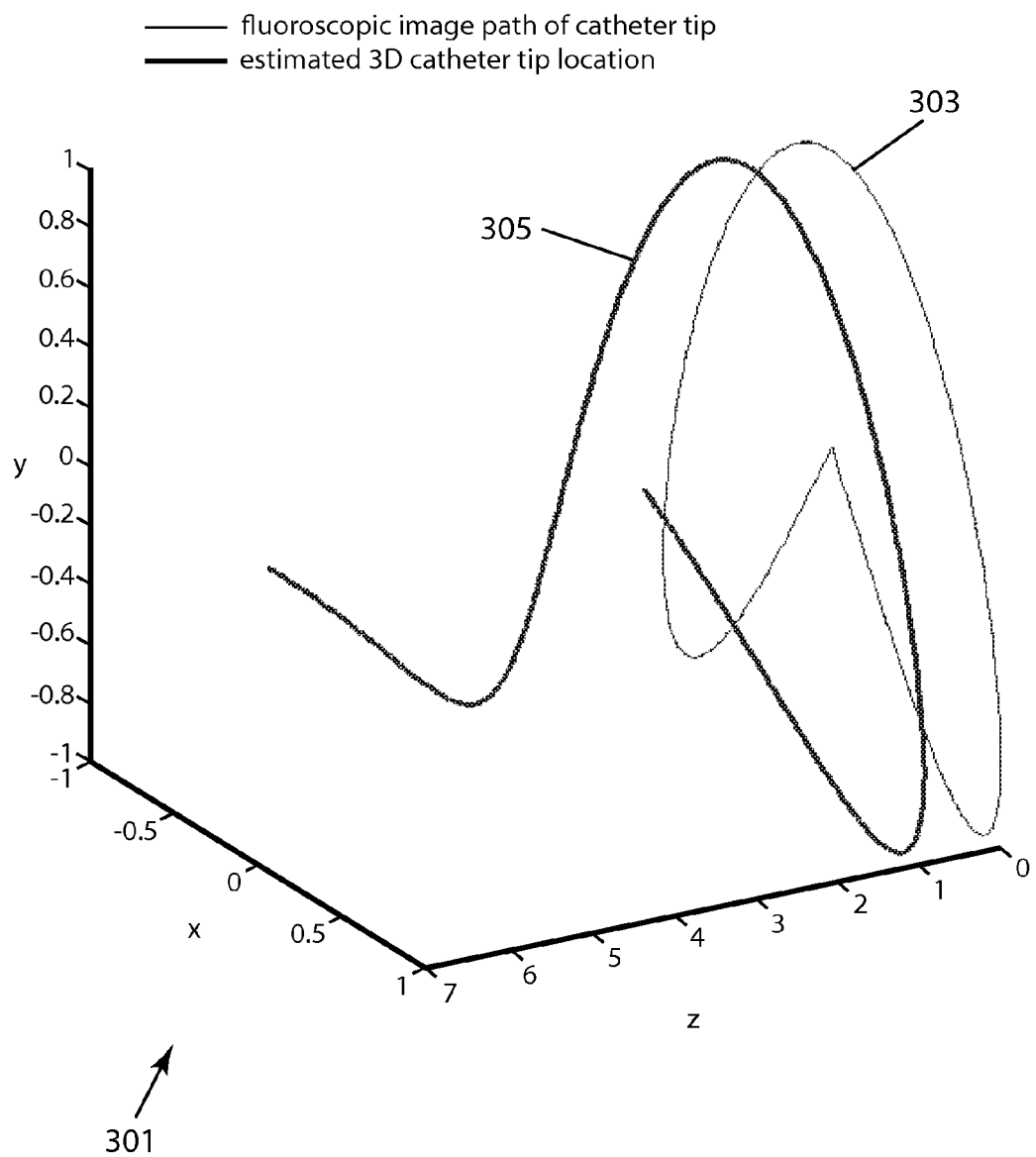
FIG. 8 is a graphical plot in perspective 3D illustrating a representative 2D fluoroscopic catheter tip path and a corresponding 3D catheter tip path according to the present invention.

FIG. 8 is a graphical plot in perspective 3D illustrating a representative 2D fluoroscopic catheter tip path 303 and a corresponding 3D catheter tip path 305 according to the present invention, shown within an x,y,z coordinate system 301. 3D catheter tip path 305 is computed using the inventive method based on single-plane fluoroscopic image data in 2D catheter tip path 303 and the algorithm described above. 2D catheter tip path 303 is in the z=0 plane of x,y,z coordinate system 301.

Figure 9:
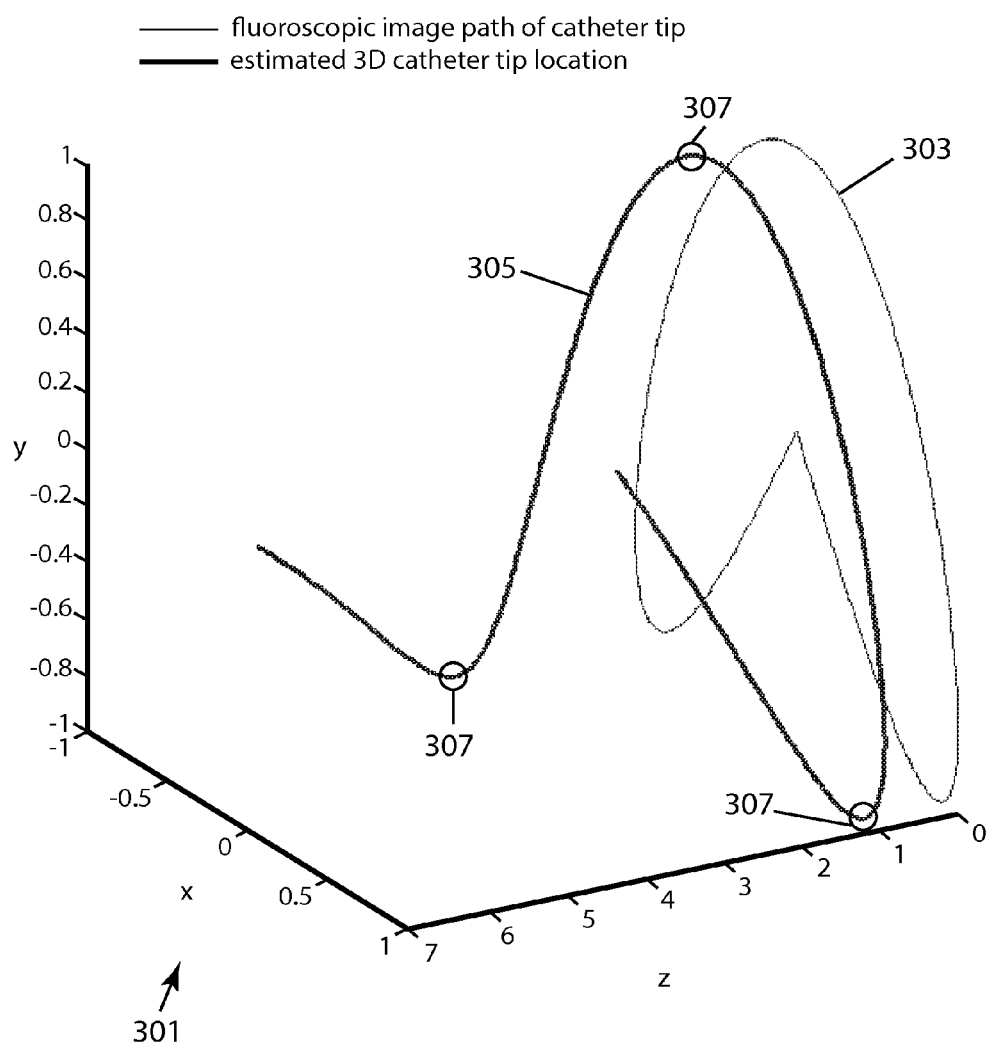
FIG. 9 is the graphical plot of FIGURE further indicating turning points in the 3D catheter tip path.

FIG. 9 is the graphical plot of FIG. 8 further indicating turning points 307 (three shown) along 3D catheter tip path 305, also shown within x,y,z coordinate system 301. Turning points 307 can be seen in FIG. 9 as points along path 305 at which one of the three coordinate values changes sign. As in FIG. 8, 2D catheter tip path 303 is in the z=0 plane of x,y,z coordinate system 301.

Figure 10:
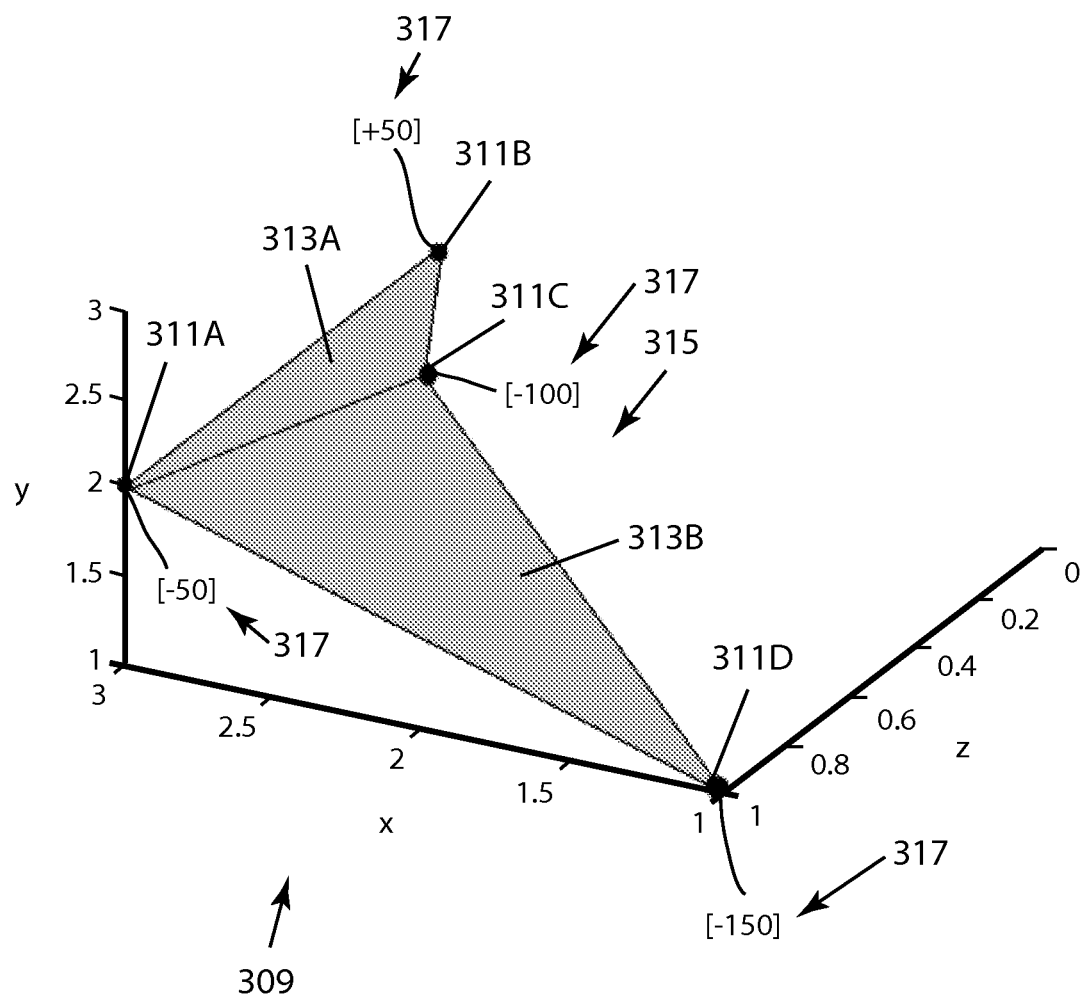
FIG. 10 is a graphical display in 3D perspective of a representative assembling of plural points into a 3D model (portion only shown) of an anatomic region of interest.

FIG. 10 is a graphical display in 3D perspective of a representative assembling of plural points into a 3D model 315 (portion only shown) of an anatomic region of interest. FIG. 10 illustrates four turning points 311A, 311B, 311C, and 311D. These four turning points 311A-D are shown within a x,y,z coordinate system 309. Turning points 311A-D are used to build a mesh model of triangular elements 313A and 313B which are then used to construct a surface of a 3D model of a anatomic region of interest. Mesh elements 313A and 313B represent interpolated surface regions within 3D model 315. FIG. 10 is simplified to show only a portion of 3D model 315 for ease of understanding.

Once a 3D model has been created, the mapping and ablation catheter can be moved over these images. Ablation points (and any other points of interest) can be marked on these images. Electrical maps such as activation maps and voltage maps derived using known techniques, such as isochronal mapping, can be used with the resulting 3D models as needed.

Referring again to FIG. 10, an overlaid electrical map is shown on the 3D model portion. Exemplary time shift values 317 in milliseconds (+ or − indicating early or later than a reference signal) are marked at points in the 3D model as the catheter is moved over the 3D model. (Time shift values 317 are shown in square brackets to differentiate these values from the reference numbers.) Such time shift values 317 are then used to guide interventional cardiac treatment procedures such as atrial fibrillation ablation.

Electrical maps can be graphically displayed in ways other than shown in FIG. 10, such as using lines of constant time shift (isochronal lines) and through the use of color-coding or other convenient graphical techniques.

While embodiments of the invention may involve a heart as an exemplary anatomical region, it will be appreciated that the invention is not so limited and that the scope of the invention may involve 3D modeling of other anatomical regions of interest within a patient. While embodiments of the invention include a mapping and ablation coronary catheter within a cardiac chamber, it will be appreciated that the invention is not so limited and that the scope of the invention includes modeling of other anatomical structures within an anatomical region. While embodiments of the invention include a catheter within the patient, it will be appreciated that the invention is not so limited and that the scope of the invention includes other devices.

The invention may be in the form of computer-implemented processes and apparatus for practicing those processes. The present invention may be embodied in a computer program having code containing instructions on tangible media, such as diskettes, CD-ROMs, hard drives, universal serial bus drives, or any other computer-readable storage media, wherein, when the computer code is loaded into and executed by a computer, the computer becomes an apparatus for practicing the invention.

While the invention has been described with reference to preferred embodiments, it will be understood by those skilled in the art that various changes may be made without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the appended claims.

The invention claimed is:

1. A method for 3D reconstruction of the positions of a catheter as it is moved within a region of a human body, comprising:
   (a) determining the initial 3D position of a point on a catheter at the start of insertion from outside the body for movement through a vein into the body region;
   (b) acquiring fixed angle, single-plane fluoroscopic 2D image data of the body region and of the catheter;
   (c) transferring the image data and catheter-point position to a computer;
   (d) determining the 2D image coordinates of the point on the catheter using the image data and the catheter-point position of step c;
   (e) changing the length of catheter insertion by a measured amount;
   (f) thereafter acquiring additional single-plane fluoroscopic image data of the body region and the catheter from the same angle, transferring the measured length change and the additional image data to the computer, and determining the 2D image coordinates of the point on the catheter;
   (g) computing the 3D position of the catheter point using only the 2D image coordinates, the measured length change, and smooth-curve assumptions about the catheter;
   (h) repeating steps e-g plural times; and
   (i) assembling the plural 3D positions of the point within the body region into a 3D model of the region,
whereby the assembled 3D positions of the point on the catheter are determined from the start of insertion and thereafter.

2. The method of claim 1 wherein the point on the catheter is the tip of the catheter.

3. The method of claim 1 wherein the acquisition of the fluoroscopic image data is ECG-gated.

4. The method of claim 3 wherein the acquisition of the fluoroscopic image data is respiration-gated.

5. The method of claim 1 further including the step of displaying the 3D model on a graphics display.

6. The method of claim 5 further including the step of displaying the 3D model overlaid simultaneously on an image of the fluoroscopic image data as the image data are transferred sequentially to the computer.

7. The method of claim 5 further including the step of interventional treatment using the catheter.

8. The method of claim 5 further including the step of creating an electrical map over the 3D model and marking points in the 3D model as the catheter is moved within the body region.

9. The method of claim 1 wherein the step of assembling the plural positions of the point within the body region into a 3D model further includes interpolating between such points.

* * * * *

UNITED STATES PATENT AND TRADEMARK OFFICE
CERTIFICATE OF CORRECTION

PATENT NO. : 8,634,896 B2  Page 1 of 1
APPLICATION NO. : 12/885710
DATED : January 21, 2014
INVENTOR(S) : Jasbir Sra et al.

It is certified that error appears in the above-identified patent and that said Letters Patent is hereby corrected as shown below:

On the title page, in the illustrative figure, in the lower-most box (to the left), delete "dat" and insert --data--.

In the Drawings

In Fig. 6, in the lower-most box (to the left), delete "dat" and insert --data--.

In the Specification

In column 2, line 11, delete "of".
In column 3, line 50, after the words invention is delete "the" and insert --to--.
In column 5, line 8, after FIGURE insert --8--.
In column 10, line 33, after the word similar, insert --to--.

Signed and Sealed this
Twenty-first Day of April, 2015

Michelle K. Lee
*Director of the United States Patent and Trademark Office*